(12) United States Patent
Huang et al.

(10) Patent No.: US 11,236,138 B2
(45) Date of Patent: *Feb. 1, 2022

(54) PEPTIDE, METHOD AND COMPOSITION FOR MELANIN POLYMERIZATION AND HAIR DARKENING

(71) Applicant: Renorigin Innovation Institute Co., Ltd., Taipei (TW)

(72) Inventors: Hsiu-Chin Huang, Taipei (TW); Hsuan Lin, Taipei (TW)

(73) Assignee: RENORIGIN INNOVATION INSTITUTE CO., LTD., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/742,270

(22) Filed: Jan. 14, 2020

(65) Prior Publication Data

US 2021/0214405 A1 Jul. 15, 2021

(51) Int. Cl.

| | | |
|---|---|---|
| *C07K 14/47* | (2006.01) |
| *A61K 8/64* | (2006.01) |
| *A61Q 5/10* | (2006.01) |
| *C07K 7/06* | (2006.01) |
| *A61Q 5/12* | (2006.01) |
| *C07K 7/08* | (2006.01) |
| *A61Q 5/02* | (2006.01) |

(52) U.S. Cl.
CPC ............ *C07K 14/4705* (2013.01); *A61K 8/64* (2013.01); *A61Q 5/02* (2013.01); *A61Q 5/10* (2013.01); *A61Q 5/12* (2013.01); *C07K 7/06* (2013.01); *C07K 7/08* (2013.01)

(58) Field of Classification Search
CPC .............................. C07K 14/4705; A61K 8/64
See application file for complete search history.

(56) References Cited

U.S. PATENT DOCUMENTS

| | | | | |
|---|---|---|---|---|
| 9,895,303 | B2 * | 2/2018 | Huang | A61Q 5/02 |
| 2002/0025537 | A1 * | 2/2002 | Bylina | G01N 33/5008 435/7.1 |
| 2003/0022821 | A1 * | 1/2003 | Svenden | A61P 35/00 514/2.5 |
| 2017/0065675 | A1 * | 3/2017 | Bancel | A61K 38/1729 |
| 2017/0239161 | A1 * | 8/2017 | Huang | A61Q 5/06 |
| 2017/0340754 | A1 * | 11/2017 | Chen | C12N 15/11 |
| 2018/0055906 | A1 * | 3/2018 | Fujii | C07K 7/06 |

* cited by examiner

*Primary Examiner* — Amber D Steele

(74) *Attorney, Agent, or Firm* — Birch, Stewart, Kolasch & Birch, LLP

(57) ABSTRACT

An isolated peptide comprises a motif of RRWQW (SEQ ID NO: 1) for melanin polymerization and hair darkening is provided. Also disclosed herein are methods and compositions for hair darkening in a mammal subject.

6 Claims, 2 Drawing Sheets
(1 of 2 Drawing Sheet(s) Filed in Color)
Specification includes a Sequence Listing.

SEQUENCE LISTING

<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<223> OTHER INFORMATION: Peptide

<400> SEQUENCE: 1

Arg Arg Trp Gln Trp
1               5

<210> SEQ ID NO 2
<211> LENGTH: 13
<212> TYPE: PRT
<213> ORGANISM: Artificial Sequence
<220> FEATURE:
<223> OTHER INFORMATION: Peptide

<400> SEQUENCE: 2

Ala Pro Arg Lys Asn Val Arg Trp Cys Thr Ile Ser Gln
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Peptide

<400> SEQUENCE: 3

Cys Thr Ile Ser Gln Pro Glu Trp Phe Lys Cys Arg Arg
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Peptide

<400> SEQUENCE: 4

Phe Lys Cys Arg Arg Trp Gln Trp
1               5

<210> SEQ ID NO 5
<211> LENGTH: 9
<212> TYPE: PRT
<213> ORGANISM: Artificial Sequence
<220> FEATURE:
<223> OTHER INFORMATION: Peptide

<400> SEQUENCE: 5

Phe Lys Cys Arg Arg Trp Gln Trp Arg
1               5

<210> SEQ ID NO 6
<211> LENGTH: 11
<212> TYPE: PRT
<213> ORGANISM: Artificial Sequence
<220> FEATURE:
<223> OTHER INFORMATION: Peptide

<400> SEQUENCE: 6

Phe Lys Cys Arg Arg Trp Gln Trp Arg Met Lys
1               5                   10

```
<210> SEQ ID NO 7
<211> LENGTH: 13
<212> TYPE: PRT
<213> ORGANISM: Artificial Sequence
<220> FEATURE:
<223> OTHER INFORMATION: Peptide

<400> SEQUENCE: 7

Phe Lys Cys Arg Arg Trp Gln Trp Arg Met Lys Lys Leu
1               5                   10

<210> SEQ ID NO 8
<211> LENGTH: 18
<212> TYPE: PRT
<213> ORGANISM: Artificial Sequence
<220> FEATURE:
<223> OTHER INFORMATION: Peptide

<400> SEQUENCE: 8

Phe Lys Cys Arg Arg Trp Gln Trp Arg Met Lys Lys Leu Gly Ala Pro
1               5                   10                  15

Ser Ile

<210> SEQ ID NO 9
<211> LENGTH: 25
<212> TYPE: PRT
<213> ORGANISM: Artificial Sequence
<220> FEATURE:
<223> OTHER INFORMATION: Peptide

<400> SEQUENCE: 9

Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25

<210> SEQ ID NO 10
<211> LENGTH: 11
<212> TYPE: PRT
<213> ORGANISM: Artificial Sequence
<220> FEATURE:
<223> OTHER INFORMATION: Peptide

<400> SEQUENCE: 10

Lys Cys Arg Arg Trp Gln Trp Arg Met Lys Lys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Peptide

<400> SEQUENCE: 11

Lys Cys Arg Arg Trp Gln Trp Arg Met Lys Lys Leu
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Peptide
```

```
<400> SEQUENCE: 12

Cys Arg Arg Trp Gln Trp Arg
1               5

<210> SEQ ID NO 13
<211> LENGTH: 11
<212> TYPE: PRT
<213> ORGANISM: Artificial Sequence
<220> FEATURE:
<223> OTHER INFORMATION: Peptide

<400> SEQUENCE: 13

Cys Arg Arg Trp Gln Trp Arg Met Lys Lys Leu
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Peptide

<400> SEQUENCE: 14

Arg Arg Trp Gln Trp Arg Met Lys Lys Leu
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Peptide

<400> SEQUENCE: 15

Arg Met Lys Lys Leu Gly Ala Pro Ser Ile
1               5                   10
```

US 11,236,138 B2

PEPTIDE, METHOD AND COMPOSITION FOR MELANIN POLYMERIZATION AND HAIR DARKENING

FIELD OF THE INVENTION

The present invention pertains to a peptide for melanin polymerization and hair darkening in mammals, and methods and compositions thereof.

BACKGROUND OF THE INVENTION

Melanin is the naturally occurring pigment and may be present in the skin, eyes, hair, feathers and scales, where they are responsible for coloration.

Melanin is characterized by irregular polymeric structures and there are two major classes of melanin, including eumelanin giving brown-black colors, and pheomelanin giving red-yellow colors, determining hair color due to their relative contents.

Because melanin is an aggregate of smaller component molecules, the extent and the distribution of the melanin aggregate/polymerization also contribute to the appearance of hair color.

BRIEF SUMMARY OF THE INVENTION

It is unexpectedly found in the present invention that a peptide effectively interacts with melanin, thereby stimulating the polymerization of melanin, wherein the peptide contains a 5-amino acid motif (RRWQW) (SEQ ID NO: 1).

It is found that a peptide having such motif is capable of stimulating melanin polymerization. In some embodiments, the peptide for stimulating melanin polymerization of the present invent is selected from the group consisting of SEQ ID NOs: 4-14.

Accordingly, in one aspect, the present invention provides an isolated peptide for increasing melanin polymerization. The isolated peptide contains a 5 amino acid motif as set forth in SEQ ID NO: 1. In some embodiments, the isolated peptide for increasing melanin polymerization is selected from the group consisting of SEQ ID NOs: 4-14.

In another aspect, the present invention provides an isolated peptide for hair darkening in a mammal subject. The isolated peptide contains a 5 amino acid motif as set forth in SEQ ID NO: 1. In some embodiments, the isolated peptide for hair darkening is selected from the group consisting of SEQ ID NOs: 4-14.

In further aspect, the present invention provides a composition for hair darkening in a mammal subject. The composition comprises an effective amount of an isolated peptide contains a 5 amino acid motif as set forth in SEQ ID NO: 1. According to certain embodiments of the invention, the composition may further comprise an acceptable carrier, and may be formulated as a topical formulation. In some embodiments, the isolated peptide is selected from the group consisting of SEQ ID NOs: 4-14 and combinations thereof.

According to the present invention, the topical formulation may comprise an ointment, an aerosol, a lotion, a cream, a gel, drops, a spray, a liquid, a patch, a shampoo or a hair conditioner. In one preferred embodiment, the composition is formulated as a shampoo or a hair conditioner.

In yet further aspect, the present invention provides a method for hair darkening in a subject in need thereof, which comprises administering to the subject the composition of the present invention in an amount effective to stimulate melanin polymerization in the subject. In preferred embodiments of the invention, the method is used to darken the hair color of the mammal subject, preferably a human subject. In preferred embodiments of the invention, the composition is administered topically to the subject.

It is to be understood that both the foregoing general description and the following detailed description are exemplary and explanatory only and are not restrictive of the invention.

BRIEF DESCRIPTION OF THE SEVERAL VIEWS OF THE DRAWINGS

The patent or application file contains at least one color drawing. Copies of this patent or patent application publication with color drawing will be provided by the USPTO upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred.

In the drawings:

Figure 1:
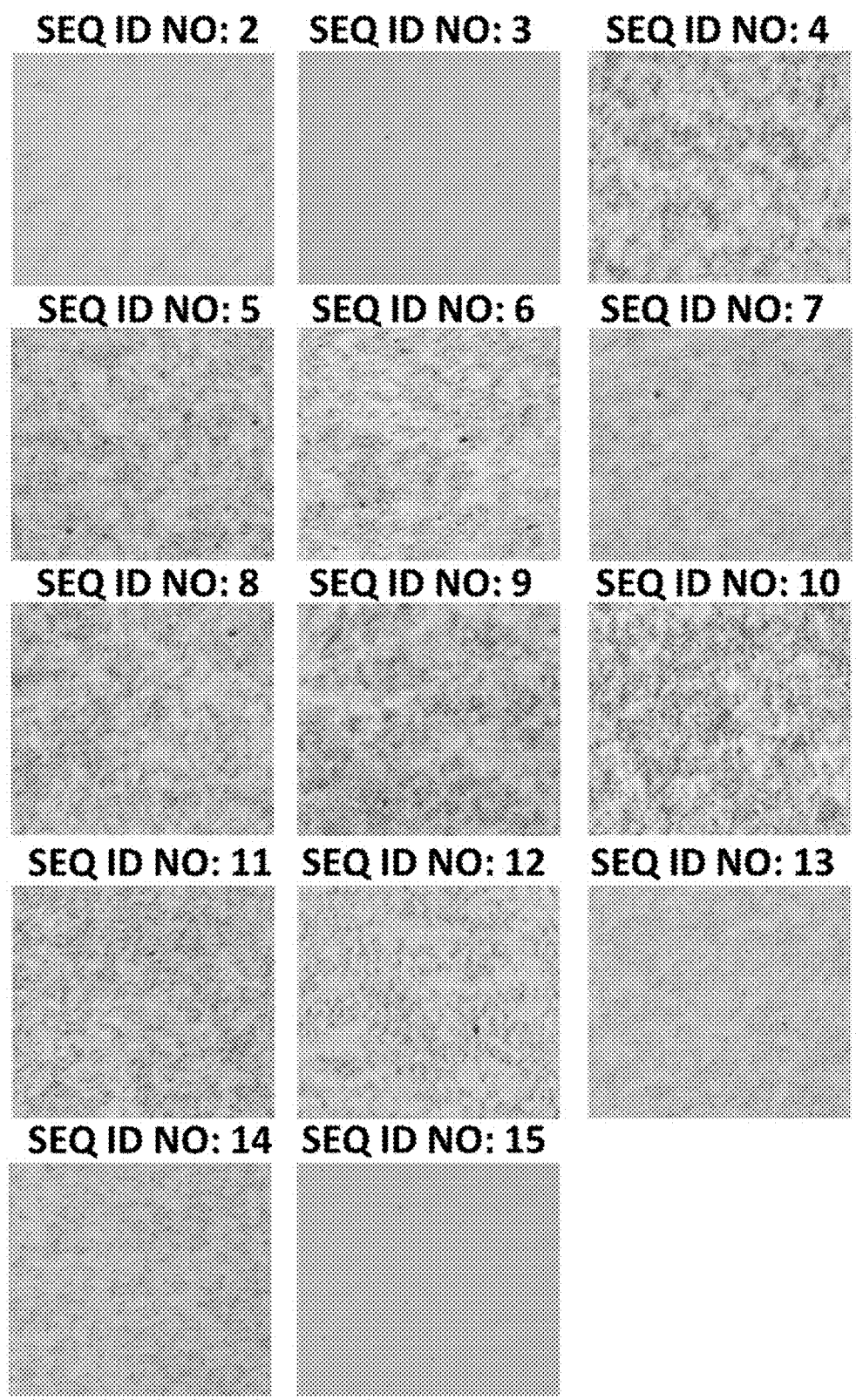

FIG. 1 shows that 0.025 mg/ml melanin was treated with 50 µM peptides in a 96-well plate for 24 h, and then photographed under a light microscope.

Figure 2:
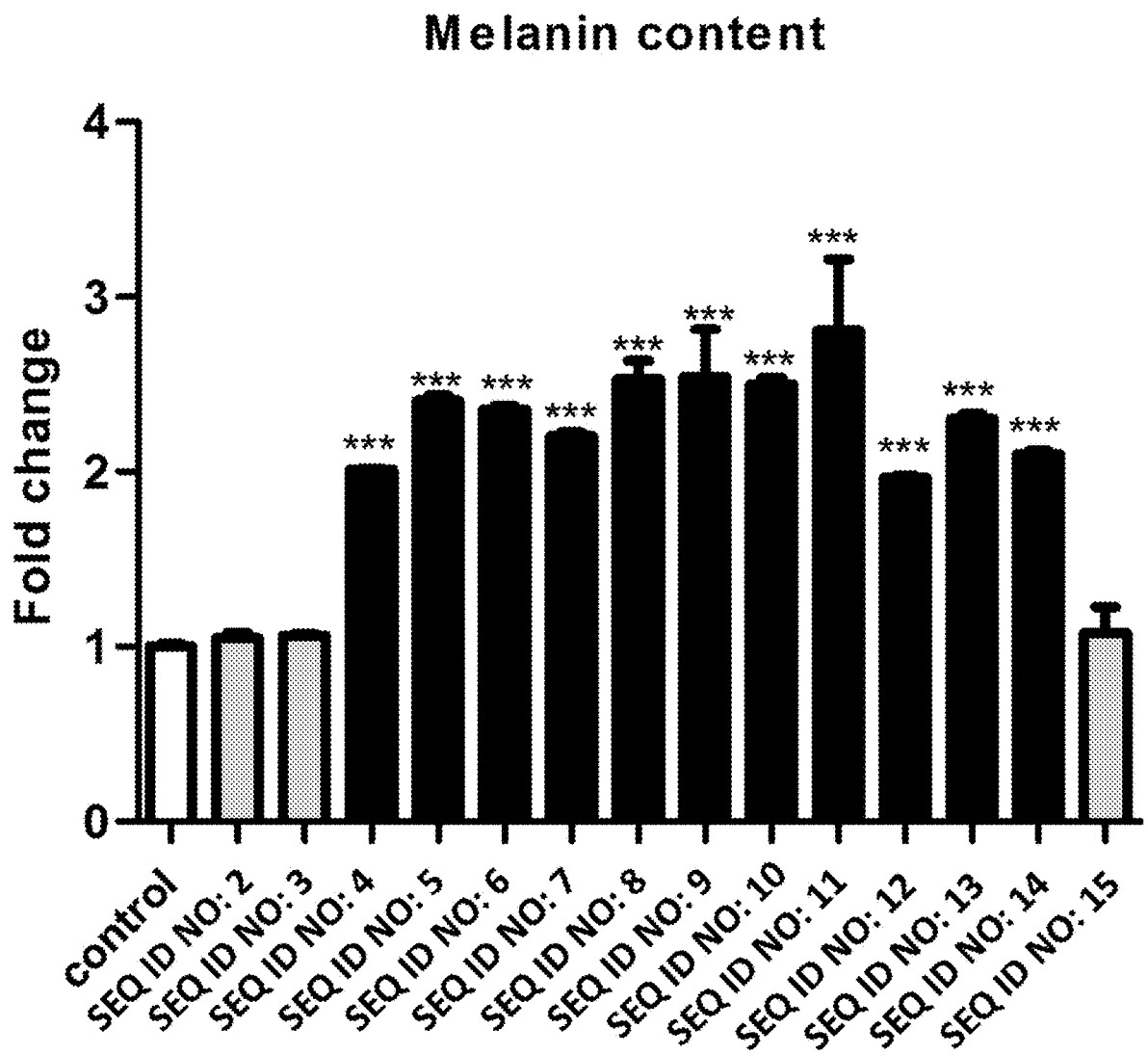

FIG. 2 shows the polymerization of melanin. 0.025 mg/ml melanin was treated with 50 µM peptide for 24 h. Data are represented as the means±SD from three independent experiments. ***$p<0.001$.

DETAILED DESCRIPTION OF THE INVENTION

Unless otherwise defined herein, scientific and technical terms used herein have the meanings that are commonly understood by those of ordinary skill in the art.

As used herein, the singular forms "a", "an", and "the" include plural referents unless the context clearly dictates otherwise. Thus, for example, reference to "a sample" includes a plurality of such samples and equivalents thereof known to those skilled in the art.

The term "hair darkening" or "darkening the hair color" as used herein refers to darkening the appearance of the hair, including, but not limited to, darkening natural hair color or restoring discolored hair due to aging (e.g., gray or white hair) or external aggressions (e.g., excess exposure to sun or chlorine).

The term "peptide" is used herein in its conventional sense, i.e., a polymer in which the monomers are amino acids and are joined together through amide bonds, alternatively referred to as a polypeptide. When the amino acids are α-amino acids, either the L-optical isomer or the D-optical isomer may be used. Additionally, unnatural amino acids, for example, β-alanine, phenylglycine and homoarginine are also meant to be included. Standard abbreviations for amino acids are used.

The term "peptide for stimulating melanin polymerization" or "peptide for hair darkening" as used herein refers to a peptide of 5 or more amino acid residues in length that has substantial melanin polymerization activity. Preferably, peptides up to about 50 amino acid residues or 40, or 30, or 25, or 20, or 15, or 10, or 6 amino acids are included in the peptide stimulating melanin polymerization.

The term "subject" as used herein can be any animal classified as a mammal, including a human.

The term "carrier" as used herein refers to materials commonly used on the formulation of pharmaceutical or cosmetic composition used to enhance stability, sterility and deliverability. When the peptide delivery system is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. The compositions may contain physiologically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The term "topical" or "topically" as used herein its conventional sense as referring to a spot which can be in or on any part of the body, including but not limited to the epidermis, any other dermis, or any other body tissue. Topical administration or application means the direct contact of the peptide with tissue, such as skin or membrane which contains melanin-producing cells.

In some embodiments, the present invention provides an isolated peptide effectively interacting with melanin, thereby stimulating the polymerization of melanin, wherein the peptide contains a 5 amino acid motif (RRWQW) (SEQ ID NO: 1). Preferably, the peptide for stimulating melanin polymerization of the present invent is selected from the group consisting of SEQ ID NOs: 4-14 and combinations thereof.

In some embodiments, the present invention provides an isolated peptide for hair darkening in a mammal subject. The isolated peptide contains a 5 amino acid motif as set forth in SEQ ID NO: 1. In some embodiments, the isolated peptide for hair darkening is selected from the group consisting of SEQ ID NOs: 4-14 and combinations thereof.

In some embodiments, the present invention provides a composition for hair darkening in a mammal subject. The composition comprises an effective amount of an isolated peptide contains a 5 amino acid motif as set forth in SEQ ID NO: 1. According to certain embodiments of the invention, the composition may further comprise an acceptable carrier, and may be formulated as a topical formulation. In some embodiments, the isolated peptide is selected from the group consisting of SEQ ID NOs: 4-14 and combinations thereof.

In some embodiments, the topical formulation may comprise an ointment, an aerosol, a lotion, a cream, a gel, drops, a spray, a liquid, a patch, a shampoo or a hair conditioner. In one preferred embodiment, the composition is formulated as a shampoo or a hair conditioner.

In some embodiments, the present invention provides a method for hair darkening in a subject in need thereof, which comprises administering to the subject the composition of the present invention in an amount effective to stimulate melanin polymerization in the subject. In preferred embodiments of the invention, the method is used to darken the hair color of the mammal subject, such as a human subject. In preferred embodiments of the invention, the composition is administered topically to the subject.

The present invention provides the use of the isolated peptide contains a 5 amino acid motif as set forth in SEQ ID NO: 1 as an active ingredient for various uses. In one preferred embodiment, the isolated peptide of the present invention is combined with an acceptable carrier to form a topical formulation which may be placed on the skin. Topical formulations may comprise an ointment, lotion, paste, cream, gel, drop, suppository, spray, liquid, shampoo, hair conditioner, powder and transdermal patch. Thickeners, diluents, emulsifiers, dispersing aids or binders may be used as needed. Preferably, one function of the carrier is to enhance skin penetration of the peptide of the present invention, and should be capable of delivering the peptide to melanocytes under in vivo conditions. Suitable carriers are well known to one of ordinary skill, and include but are not limited to water, dimethylsulfoxide, ethanol, liposome, liquid petrolatum, petrolatum dimethylformamide, 2-pyrrolidone, oleic acid, and Azone® brand penetration enhancer.

The present invention is further illustrated by the following examples, which are provided for the purpose of demonstration rather than limitation.

EXAMPLES

1. Sample Preparation

All peptides (Table 1) were synthesized by Genomics Bioscience & Technology co. Ltd (Taipei, Taiwan) and the purity and composition of these peptides was confirmed by high performance liquid chromatography (HPLC) and mass spectrometry. Peptide stocks were prepared by dissolving 10 mg of lyophilized peptide powder in 1 ml of double deionized water (ddH2O), and then stored at −20° C. Melanin was purchased from Sigma-Aldrich (St. Louis, Mo., USA).

TABLE 1

Library of synthesized peptides

| Name | Sequence |
|---|---|
| SEQ ID NO: 2 | APRKNVRWCTISQ |
| SEQ ID NO: 3 | CTISQPEWFKCRR |
| SEQ ID NO: 4 | FKCRRWQW |
| SEQ ID NO: 5 | FKCRRWQWR |
| SEQ ID NO: 6 | FKCRRWQWRMK |
| SEQ ID NO: 7 | FKCRRWQWRMKKL |
| SEQ ID NO: 8 | FKCRRWQWRMKKLGAPSI |
| SEQ ID NO: 9 | FKCRRWQWRMKKLGAPSITCVRRAF |
| SEQ ID NO: 10 | KCRRWQWRMKK |
| SEQ ID NO: 11 | KCRRWQWRMKKL |
| SEQ ID NO: 12 | CRRWQWR |
| SEQ ID NO: 13 | CRRWQWRMKKL |
| SEQ ID NO: 14 | RRWQWRMKKL |
| SEQ ID NO: 15 | RMKKLGAPSI |

2. The Polymerization of Melanin 0.025 mg/ml melanin were treated with 50 μM peptides for 24 h, and then centrifuged at 10,000 g for 5 min. The supernatant was removed from the tube, leaving only the melanin pellet. The polymerization of melanin was quantified after boiling in 1 M NaOH for 1 hour and the absorbance was measured spectrophotometrically at 400 nm.

Results

Melanin treated with 50 μM peptides, which contain RRWQW (SEQ ID NO: 1) motif as shown in Table 1, showed significantly melanin polymerization. However, SEQ ID NOs: 2, 3 and 15 did not show effects on melanin polymerization (FIGS. 1 and 2).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A composition for hair darkening in a mammalian subject, comprising an effective amount of a peptide selected from the group consisting of:
   a peptide consisting of SEQ ID NO: 4,
   a peptide consisting of SEQ ID NO: 5,
   a peptide consisting of SEQ ID NO: 6,
   a peptide consisting of SEQ ID NO: 7,
   a peptide consisting of SEQ ID NO: 9,
   a peptide consisting of SEQ ID NO: 10,
   a peptide consisting of SEQ ID NO: 11,
   a peptide consisting of SEQ ID NO: 12,
   a peptide consisting of SEQ ID NO: 13 and
   a peptide consisting of SEQ ID NO: 14;
   which is formulated as a topical formulation in a form of an ointment, an aerosol, a lotion, a cream, a gel, drops, a spray, a patch, a shampoo or a hair conditioner.

2. The composition of claim 1, further comprising a physiologically acceptable carrier.

3. The composition of claim 1, wherein the topical formulation is a shampoo.

4. The composition of claim 1, wherein the topical formulation is a hair conditioner.

5. The composition of claim 1, wherein the topical formulation is a spray.

6. A method for hair darkening in a subject, comprising administering to the subject an effect amount of the composition of claim 1 to stimulate melanin polymerization in the subject.

* * * * *